US007833533B2

United States Patent
Grubman et al.

(10) Patent No.: US 7,833,533 B2
(45) Date of Patent: Nov. 16, 2010

(54) ENHANCED ANTIVIRAL ACTIVITY AGAINST FOOT AND MOUTH DISEASE

(75) Inventors: Marvin J. Grubman, Southold, NY (US); Marla J. Koster, Cutchogue, NY (US); Mauro Moraes, Old Saybrook, CT (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/109,020

(22) Filed: Apr. 24, 2008

(65) Prior Publication Data

US 2009/0269372 A1    Oct. 29, 2009

(51) Int. Cl.
*A61K 39/125*    (2006.01)
(52) U.S. Cl. .................. 424/216.1; 435/320.1
(58) Field of Classification Search ........................ None
See application file for complete search history.

(56) References Cited

OTHER PUBLICATIONS

Yao et al, Veterinary immunology and Immunopathology, Available on-line as of Oct. 2, 2007, vol. 122, pp. 309-311.*
Chinsangaram et al, Journal of Virology, 2003, vol. 77, No. 2, pp. 1621-1625.*
Moraes et al, Journal of Virology, Jul. 2007, vol. 81, No. 13, pp. 7124-7135.*

* cited by examiner

*Primary Examiner*—Ali R. Salimi
(74) *Attorney, Agent, or Firm*—John D. Fado; Evelyn M. Rabin

(57) ABSTRACT

Previously, we showed that type I interferon (alpha/beta interferon [IFN-$\alpha/\beta$]) can inhibit foot-and-mouth disease virus (FMDV) replication in cell culture, and swine inoculated with $10^9$ PFU of human adenovirus type 5 expressing porcine IFN-$\alpha$ (Ad5-pIFN-$\alpha$) were protected when challenged 1 day later. In this study, we found that type II pIFN (pIFN-$\gamma$) also has antiviral activity against FMDV in cell culture and that, in combination with pIFN-$\alpha$, it has a synergistic antiviral effect. We also observed that while each IFN alone induced a number of IFN-stimulated genes (ISGs), the combination resulted in a synergistic induction of some ISGs. To extend these studies to susceptible animals, we inoculated groups of swine with a control Ad5, $10^8$ PFU of Ad5-pIFN-$\alpha$, low- or high-dose Ad5-pIFN-$\gamma$, or a combination of Ad5-pIFN-$\alpha$ and low- or high-dose Ad5-pIFN-$\gamma$ and challenged all groups with FMDV 1 day later. The control group and the groups inoculated with either Ad5-pIFN-$\alpha$ or a low dose of Ad5-pIFN-$\gamma$ developed clinical disease and viremia. However, the group that received the combination of both Ad5-IFNs with the low dose of Ad5-pIFN-$\gamma$ was completely protected from challenge and had no viremia. Similarly the groups inoculated with the combination of Ad5s with the higher dose of Ad5-pIFN-$\gamma$ or with only high-dose Ad5-pIFN-$\gamma$ were protected. The protected animals did not develop antibodies against viral nonstructural (NS) proteins, while all infected animals were NS protein seropositive. No antiviral activity or significant levels of IFNs were detected in the protected groups, but there was an induction of some ISGs. The results indicate that the combination of type I and II IFNs act synergistically to inhibit FMDV replication in vitro and in vivo.

9 Claims, 3 Drawing Sheets

A

B

SEQUENCE LISTING

<160> NUMBER OF SEQ ID NOS: 41

<210> SEQ ID NO 1
<211> LENGTH: 41
<212> TYPE: DNA
<213> ORGANISM: Artificial Sequence
<220> FEATURE:
<223> OTHER INFORMATION: Chemically Synthesized

<400> SEQUENCE: 1
ctagcgatcg atgagttata caacttattt cttagctttt c         41

<210> SEQ ID NO 2
<211> LENGTH: 41
<212> TYPE: DNA
<213> ORGANISM: Artificial Sequence
<220> FEATURE:
<223> OTHER INFORMATION: Chemically Synthesized

<400> SEQUENCE: 2
tgcagtctag attattttga tctctctgcc cttggaacat a         41

<210> SEQ ID NO 3
<211> LENGTH: 20
<212> TYPE: DNA
<213> ORGANISM: Artificial Sequence
<220> FEATURE:

<223> OTHER INFORMATION: Chemically Synthesized

<400> SEQUENCE: 3
cgtccctgag acacgatggt          20

<210> SEQ ID NO 4
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 4
cccgatgcgg ccaaat          16

<210> SEQ ID NO 5
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 5
aaggtcggag tgaacg          16

<210> SEQ ID NO 6
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 6
gcattcgtat tgcgccg          17

<210> SEQ ID NO 7
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 7
ccgtcttgcg ccggt          15

<210> SEQ ID NO 8
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 8
caagaatttc acctcta          17

<210> SEQ ID NO 9
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 9
gaggtggacc ccgaagga          18

```
<210> SEQ ID NO 10
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 10
caccagatcc ggcttcgt                                                   18

<210> SEQ ID NO 11
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 11
aggaccatcg ggatc                                                      15

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 12
ctgtcgttgg acgatgtatg ct                                              22

<210> SEQ ID NO 13
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 13
cagccgggtc cagaatca                                                   18

<210> SEQ ID NO 14
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 14
tcaagaaacc caggcct                                                    17

<210> SEQ ID NO 15
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 15
tggtgcatga gatgctcca                                                  19

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized
```

```
<400> SEQUENCE: 16
ccaaatccac ctgagccaat t                                              21

<210> SEQ ID NO 17
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 17
ccaggtttgt cgaagat                                                   17

<210> SEQ ID NO 18
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 18
tggtgcatga gatgctcca                                                 19

<210> SEQ ID NO 19
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 19
gccgagccct ctgtgct                                                   17

<210> SEQ ID NO 20
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 20
cagaccttcc aagctct                                                   17

<210> SEQ ID NO 21
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 21
aagtgcatcc tccaaatcgc t                                              21

<210> SEQ ID NO 22
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 22
gctcatggaa agagctgtgg                                                20

<210> SEQ ID NO 23
<211> LENGTH: 15
```

```
<212> TYPE: DNA
<213> ORGANISM: Artificial Sequence
<220> FEATURE:
<223> OTHER INFORMATION: Chemically Synthesized

<400> SEQUENCE: 23
tcctgatgtg ttctc                                                      15

<210> SEQ ID NO 24
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 24
tggcagcagt cgtctttatc a                                               21

<210> SEQ ID NO 25
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 25
cccgcaccca tttcttctc                                                  19

<210> SEQ ID NO 26
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 26
tggcacacac ctggcggttc tttc                                            24

<210> SEQ ID NO 27
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 27
tggtagctct gggaaactga atg                                             23

<210> SEQ ID NO 28
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 28
ggctttgcgc tggatctg                                                   18

<210> SEQ ID NO 29
<211> LENGTH: 38
<212> TYPE: DNA
<213> ORGANISM: Artificial Sequence
<220> FEATURE:
<223> OTHER INFORMATION: Chemically Synthesized

<400> SEQUENCE: 29
```

-continued cttcgaaaag ctgattaaaa ttccggtaga taatctgc    38

<210> SEQ ID NO 30
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 30
cgttatgcca ccaacaatgg    20

<210> SEQ ID NO 31
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 31
agacccggaa gtcgtgctt    19

<210> SEQ ID NO 32
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 32
atcaggtcgg ccatcaccgt g    21

<210> SEQ ID NO 33
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 33
ctggtttcgc tattggtgga a    21

<210> SEQ ID NO 34
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 34
gcatccaggt cttcacactg tatt    24

<210> SEQ ID NO 35
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 35
ctgcaatcaa ggtgatcccc actctattca    30

<210> SEQ ID NO 36
<211> LENGTH: 23
<212> TYPE: DNA
<213> ORGANISM: Artificial Sequence

```
<220> FEATURE:
<223> OTHER INFORMATION: Chemically Synthesized

<400> SEQUENCE: 36
aatccagccc tgataccttc tct                                               23

<210> SEQ ID NO 37
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 37
ggcctgttca atgtccaagt c                                                 21

<210> SEQ ID NO 38
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 38
tgcctgatga ccacagcagc tacaca                                            26

<210> SEQ ID NO 39
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 39
ttgaaatgat tcctgcaagt caa                                               23

<210> SEQ ID NO 40
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 40
gacatctttt ctccccattc tttt                                              24

<210> SEQ ID NO 41
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 41
cttgcccaca tgttgagatc attgccac                                          28
```

ENHANCED ANTIVIRAL ACTIVITY AGAINST FOOT AND MOUTH DISEASE

BACKGROUND OF THE INVENTION

1. Field of the Invention

This invention relates to an antiviral pharmaceutical composition comprising a combination of a vector containing the gene encoding porcine interferon-γ (pIFN-γ) and a vector containing the gene encoding porcine interferon-α (pIFN-α), wherein the composition is capable of synergistically blocking foot and mouth disease virus (FMDV) replication in vivo, and thereby acting synergistically to protect swine, bovines, goats, and sheep against FMDV challenge at doses that do not protect against FMDV challenge when administered alone and to the method of treating swine, bovines, goats, and sheep with the antiviral composition of the invention in order to reduce the degree or rate of infection by FMDV, to reduce the severity of foot and mouth disease (FMD) or any symptom or condition resulting from infection by the FMDV in the treated animal as compared to an untreated infected animal, and preferably, to protect swine, bovines, goats, and sheep against clinical FMD.

2. Description of the Relevant Art

Foot-and-mouth disease virus (FMDV), a member of the Picornaviridae family, is the most contagious pathogen of cloven-hoofed animals including bovines, swine, sheep, and goats, and causes a rapidly-spreading, acute infection characterized by fever, lameness and vesicular lesions on the feet, tongue, snout and teats (Grubman and Baxt. 2004. *Clinical Micro. Rev.* 17: 465-493). In areas where FMD is enzootic, disease control is achieved by slaughter of infected animals, movement control of susceptible animals, and vaccination. The current vaccine, an inactivated whole virus antigen, is not ideally suited to eliminate FMD outbreaks from previously disease-free countries since vaccinated animals cannot be unequivocally differentiated from infected animals. As a result FMD-free countries do not import animals or animal products from countries that use this vaccine, and in the event of an outbreak in disease-free countries, the most rapid method of regaining FMD-free status and resuming international trade is to slaughter infected and susceptible animals that have been in contact with infected animals. After the 2001 FMD outbreaks in the United Kingdom and The Netherlands, it became apparent that this practice is opposed by the public. International organizations such as the Office International des Epizooties (OIE) and the world organization for animal health, as well as meat-exporting countries, now support the development and use of marker vaccines and companion diagnostic tests that will allow differentiation of vaccinated from infected animals in FMD control programs (2002. The Royal Society, London, United Kingdom; Scudamore and Harris. 2002. *Rev. Sci. Tech. Off Int. Epiz.* 21: 699-710). We have recently developed a novel marker FMD vaccine candidate delivered by a recombinant, replication-defective human; adenovirus type 5 vector (Ad5-FMD) that can protect both swine and cattle (Mayr et al. 1999. *Virology* 263: 496-506; Moraes et al. 2002. *Vaccine* 20: 1631-1639; Pacheco et al. 2005. *Virology* 337: 205-209).

More recently the above-named organizations have also come to realize that to be successful, FMD control programs should include rapid measures to limit and control disease spread. To meet these needs, they now support the development of antivirals and/or immunomodulatory molecules (2002. The Royal Society, supra).

The innate immune system provides the initial response of the host to pathogen invasion (Biron and Sen. 2001. In: *Fields Virology*, 4$^{th}$ Edition, Knipe et al. (eds), Lippincott Williams & Wilkins, Philadelphia, Pa., pages 321-351). Type I interferons (alpha/beta interferons [IFN-α/β]) are rapidly induced after virus infection and via a series of events; in paracrine and autocrine processes, they lead to the expression of hundreds of gene products some of which have antiviral activity (Der et al. 1998. *Proc. Natl. Acad. Sci. USA* 95: 15623-15628). However, like other viruses, FMDV has evolved multiple mechanisms to overcome the IFN-α/β response (Basler and Garcia-Sastre. 2002. *Int. Rev. Immunol.* 21: 305-337; Conzelmann, K.-K. 2005. *J. Virol.* 79: 5241-5248; de los Santos et al. 2006. *J. Virol.* 80: 1906-1914; Devany et al. 1988. *J. Virol.* 62: 4407-4409; Goodbourn et a/2000. *J. Gen. Virol.* 81: 2341-2364; Katze et al. 2002. *Nat. Rev. Immunol.* 2: 675-687; Weber et al. 2004. *Viral Immunol.* 17: 498-515). Nevertheless, we and others have shown that pretreatment of cells with IFN-α/β can dramatically inhibit FMDV replication (Ahl and Rump. 1976. *Infect. Immun.* 14: 603-606; Chinsangaram et al. 2001. *J. Virol.* 75: 5498-5503; Chinsangaram et al. 1999. *J. Viral.* 73: 9891-9898) and at least two IFN-α/β-stimulated gene products (ISGs), double-stranded RNA-dependent protein kinase (PKR) and 2'-5' oligoadenylate synthetase (OAS)/RNase L, are involved in this process (Chinsangaram et al. 2001, supra; de los Santos et al., supra). Based on these observations, we previously constructed an Ad5 vector containing the porcine IFN-α gene (Ad5-pIFNα) as a possible method of rapidly inducing protection against FMD. Ad5-pIFNα produces high levels of biologically active IFN in infected-cell supernatants (Chinsangaram et al. 2003. *J. Virol.* 77: 1621-1625). Swine inoculated with Ad5-pIFNα are protected when challenged with FMDV one day later, and protection can last for 3 to 5 days (Chinsangaram et al. 2003, supra; Moraes et al. 2003. *Vaccine* 22: 268-279). Protection correlates with an increase in the amount of IFN-α protein in serum and the induction of PKR and OAS mRNA in white blood cells (Chinsangaram et al. 2003, supra; de Avila Botton et al. 2006. *Vaccine* 24: 3446-3456; Moraes et al. 2003, supra). However, since this approach has not been completely effective for cattle (Wu et al. 2003. *J. Interferon Cytokine Res.* 23: 371-380), we are attempting to identify new strategies to induce rapid protection.

Type II IFN (IFN-γ) is a multifunctional cytokine produced by T-helper 1 (Th1) and natural killer (NK) cells, and its biological functions include immunoregulatory, anti-neoplastic, and antiviral properties (Biron and Sen, supra). The antiviral effect of IFN-γ may be direct (intracellular) or indirect, involving effector cells of the immune system (Chesler and Reiss. 2002. *Cytokine Growth Factor Rev.* 13: 441-454). The antiviral activity of IFN-γ against several viruses, including herpes simplex virus, hepatitis C virus, West Nile virus, vaccinia virus, vesicular stomatitis virus (VSV), human immunodeficiency virus, and coxsackievirus, another member of the picornavirus family, has been demonstrated (Cantin et al. 1999. *J. Virol.* 73: 3418-3423; Frese et al. 2002. *Hepatology* 35: 694-703; Hartshorn et al. 1987. *AIDS Res. Hum. Retroviruses* 3: 125-133; Henke et al. 2001. *J. Virol.* 75:8187-8194; Henke et al. 2003. *Virology* 315: 335-344; Horwitz et al. 1999. *J. Virol.* 73: 1756-1766; Karupiah et al., 1990. *J. Exp. Med.* 172: 1495-1503; Komatsu et al. 1996. *J. Neuroimmunol.* 68: 101-108; Shrestha et al. 2006. *J. Virol.* 80: 5338-5348). Recently, indoleamine 2,3-dioxygenase (INDO) (Adams et al., 2004. *J. Virol.* 78: 2632-2636; Bodaghi et al. 1999. *J. Immunol.* 162: 957-964; Obojes et al., 2005. *J. Virol.* 79: 7768-7776) and inducible nitric oxide synthase (iNOS) (Saura et al. 1999. *Immunity* 10: 21-28; Zaragoza et al. 1997.

J. Clin. Invest. 100: 1760-1767) have been identified as IFN-γ-induced gene products that have intracellular antiviral effects.

Although the signal transduction pathways elicited by each type of IFN differ, the combination of type I and type II IFNs can synergistically induce gene expression (Cheney et al. 2002. J. Virol. 76: 11148-11154; Levy et al. 1990. EMBO J. 9: 1105-1111; Matsumoto et al. 1999. Biol. Chem. 380: 699-703; Thomas and Samuel. 1992. J. Virol. 66: 2519-2522). The coactivation of the IFN signaling pathways produce an increased effect in blocking the replication of a number of viruses in vitro and/or in vivo, including coronavirus (Sainz et al. 2004. Virology 329: 11-17), herpes simplex virus (Balish et al. 1992. J. Infect. Dis. 166: 1401-1403; Sainz and Halford. 2002. J. Virol. 76: 11541-11550; Vollstedt et al. 2004. J. Virol. 78: 3846-3850), varicella-zoster virus (Desloges et al. 2005. J. Gen. Virol. 86: 1-6), cytomegalovirus (CMV; Sainz et al. 2005. Virol. J. 23: 2-14), vaccinia virus (Liu et al. 2004. FEMS Immunol. Med. Microbiol. 40: 201-206), hepatitis C virus (Okuse et al. 2005. Antiviral Res. 65: 23-34), and mouse hepatitis virus (Fuchizaki et al. 2003. J. Med. Virol. 69: 188-194).

Here, we have evaluated the antiviral effect of IFN-γ on FMDV replication and determined that a combination of IFN-α and IFN-γ can act synergistically to block FMDV replication. Constructs comprising the genes encoding pIFN-γ and pIFN-α, e.g., in separate constructs or together in one construct provide a means to deliver IFN protein, allowing animals to produce IFN-γ and IFN-α endogenously. Vectors, such as recombinant replication-defective human adenoviruses, comprising these genes are effective for delivery and expression in vivo. Here, we demonstrate the antiviral properties of IFN-γ and the synergistic effect of a combination of pIFN-α and pIFN-γ on FMDV replication in cell culture. Furthermore, our in vivo experiments indicate that swine inoculated with vectors comprising pIFN-γ and pIFN-α, at doses that alone do not protect against FMDV challenge, are completely protected against clinical disease and do not develop viremia or antibodies against viral nonstructural (NS) proteins.

SUMMARY OF THE INVENTION

We have discovered that a vector containing the porcine IFN-γ gene has anti-FMDV properties and that a combination of pIFN-α and pIFN-γ acts synergistically to block FMDV replication in cell culture and in vivo.

In accordance with this discovery, it is an object of the invention to provide constructs and vectors containing the porcine IFN-γ gene and porcine IFN-α gene and to protect animals susceptible to FMDV from clinical disease by inoculating such animals with vectors comprising these genes and in particular, inoculating animals with the combination of these genes at those doses which alone do not protect against FMDV challenge, but which when given together, are effective for ensuring early protection against FMDV challenge.

An added object of the invention is to provide immunogenic compositions comprising constructs and vectors comprising pIFN-γ and pIFN-α in combination.

An additional object of the invention is to provide a rationally designed live FMDV vaccine comprising genes encoding pIFN-γ and pIFN-α together with Ad5-FMDV or another effective FMDV vaccine.

A further object of the invention is to provide a marker vaccine which allows a serological distinction between vaccinated animals and animals infected with FMDV.

Another object of the invention is to provide a method for protecting an animal against FMDV by administering an effective amount of a composition comprising a vector containing a gene encoding pIFN-γ and a vector containing a gene encoding pIFN-α.

Yet another object of the invention is to provide a method for protecting an animal against FMDV by administering an effective amount of the marker vaccine comprising pIFN-γ and pIFN-α and Ad5-FMDV.

It is an object of the invention to protect swine, cows, goats, and sheep from FMDV replication and FMD.

An additional object of the invention is to provide a method for delaying onset or severity of FMDV in an animal by administering an effective amount of a composition comprising a vector containing a gene encoding pIFN-γ and a vector containing a gene encoding pIFN-α.

An additional object of the invention is to provide a method for delaying onset or severity of FMDV in an animal by administering an effective amount of the marker vaccine comprising pIFN-γ and pIFN-α and Ad5-FMDV.

Other objects and advantages of this invention will become readily apparent from the ensuing description.

BRIEF DESCRIPTION OF THE DRAWINGS

FIG. 2A depicts cells that were pretreated for 24 h with various amounts of pIFN-α or pIFN-γ and 24 h later infected with FMDV. After a 1 h adsorption, the cells were rinsed with 150 mM NaCl-20 mM MES (pH 6) and with MEM. Supernatants were collected at 1 and 24 h p.i. and titrated on BHK-21 cells. The results are expressed as the virus titer (number of PFU per ml) at 24 h p.i. after subtracting the titers at 1 h p.i. FIG. 2B depicts cells that were pretreated with 1 or 2 units of pIFN-plus increasing amounts of pIFN-γ and 24 h later infected with FMDV as described above. The results are expressed as the virus titer (number of PFU per ml) at 24 h p.i. after subtraction of the titers at 1 h p.i.

DETAILED DESCRIPTION OF THE INVENTION

Figure 1:
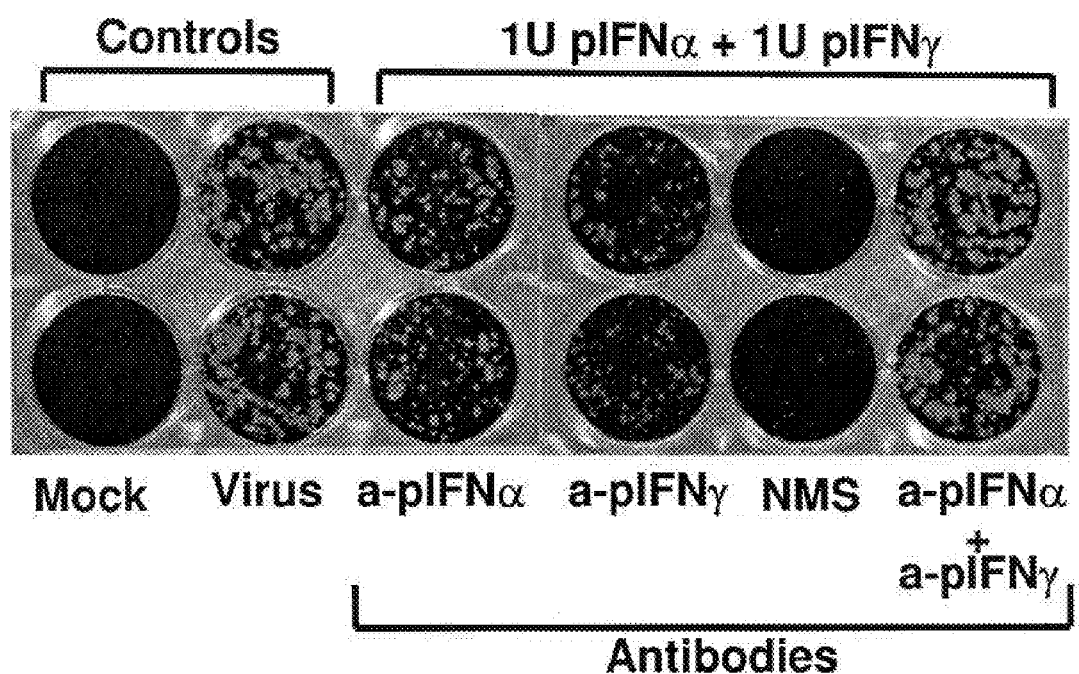
FIG. 1 depicts the neutralization of IFN activity by monoclonal antibodies (MAbs). MAbs K9 against pIFN-α (a-pIFN-α) and P2C11 against pIFN-γ (a-pIFN-γ) as well as normal mouse serum (NMS) were diluted 1:500 and incubated individually or together for 1 h at RT with 1 unit of pIFN-α and 1 unit of pIFN-γ. Treated or untreated pIFNs were incubated with IBRS-2 cells for 24 h and infected with approximately 100 plaques of FMDV. Plaques were detected by crystal violet staining.

We have previously demonstrated that FMDV replication is inhibited by the pretreatment of cells with IFN-α/β and that swine inoculated with Ad5-pIFN-α are protected from clinical disease and virus replication when challenged 1 day later (Chinsangaram et al. 2001, 2003, supra). However, we found that this approach is only partially effective for cattle (Wu et al., supra). To improve the ability to rapidly limit and/or block FMDV replication in susceptible animals, we examined the potential of a combination of IFN-α/β and IFN-γ as a treatment strategy for FMD. It has been demonstrated that this combination can synergistically inhibit the replication of a number of viruses in cell culture (Balish et al., Deslogues et al., Okuse et al., Sainz Jr. et al. 2005, 2004, supra) and can also result in improved responses to virus infection in various animal models (Fuchizaki et al., Liu et al., Sa-Carvalho et al., Vollstedt et al., supra). Our data demonstrate that in cell culture, the combination approach synergistically blocked FMDV replication and that treated swine were sterilely protected from virus challenge.

To examine the effect of IFN-γ on FMDV replication in cell culture, we constructed an Ad5 vector containing the pIFN-γ gene. We found that supernatants obtained from cells infected with this virus have antiviral activity against FMDV in porcine cells. This antiviral activity is pIFN-γ-specific since it is inhibited by a MAb directed against pIFN-γ. These results support previous data from Zhang et al. (2002. *Arch. Virol.* 147: 2157-2167) which showed that pretreatment of primary bovine thyroid cells with bovine IFN-γ profoundly reduced FMDV RNA and protein synthesis. Furthermore, we found that compared with the results of individual treatments, the combination of pIFN-α and pIFN-γ synergistically reduced both plaque number and virus yield (Table 2 and FIG. 2B, See Example 4).

We have previously shown that two IFN-α-stimulated gene products, PKR and OAS, are involved in the inhibition of FMDV replication (Chinsangaram et al. 2001, de los Santos et al., supra). To understand the basis of the IFN-γ-induced inhibition of FMDV replication as well as the mechanism of the synergistic antiviral activities of the combined IFNs, we examined the effect of these treatments in cell culture on known IFN-stimulated genes. Since the swine genome has not yet been completely determined, we selected well-characterized genes that have been shown to be induced by IFN-α, i.e., Mx1, OAS, PKR, and RANTES, as well as by IFN-γ, i.e., INDO, iNOS, IP-10 (the 10-kDa IFN-γ-inducible protein), and IRF1. In cells treated with IFNs, the mRNAs for the above-named genes were significantly induced, while in cells infected with the combination Ad5s, we also observed a two- to fourfold synergistic induction of expression of INDO and IP-10 as well as an approximately two- to threefold synergistic increase in Mx1 and OAS at 48 h p.i. (Table 4).

To extend these studies to animals, we selected doses of each Ad5 vector that individually would not protect against FMDV challenge but combined would limit or preferably block clinical disease. Based on previous animal experiments, we selected a dose of $10^8$ PFU of Ad5-CI-pIFN-α/animal (Chinsangaram et al., 2003, supra), while our selection of a dose of Ad5-CI-pIFN-γ was the result of the cell culture expression studies (Table 1).

It has been shown by Muruve and coworkers (Muruve, D. A. 2004. *Human Gene Therapy* 15: 1157-1166; Muruve et al. 1999. *Human Gene Therapy* 10: 965-976) that the Ad5 particle can rapidly induce an innate immune response which is transient and dose dependent. We have also previously found that swine inoculated with a control Ad5 vector developed an antiviral response and detectable IFN-α at 4 h p.i., which peaked at 10 h p.i. and was absent by 24 h (Moraes et al., 2003, supra). Therefore, to compensate for the potential antiviral effect induced by the vector alone, we inoculated all animals with the same dose of Ad5 utilizing a control Ad5 vector, Ad5-VSVG, to adjust the total dose.

Groups administered the control virus (Ad5-VSVG), Ad5-CI-pIFN-α alone, or the low dose of Ad5-CI-pIFN-γ developed clinical disease and viremia, but in all animals in the last two groups, viremia was approximately 10-fold lower than in the control group and lasted for a shorter time, and the onset of clinical disease was generally delayed (Table 5). Most significantly, the combination of $10^8$ PFU of Ad5-CI-pIFN-α and $10^9$ PFU of Ad5-CI-pIFN-γ, which individually did not protect, induced complete protection in all animals. Furthermore, the animals in this group did not have detectable viremia or virus in nasal swab specimens and did not develop antibodies against the viral NS proteins, as determined by a number of assays (Table 6). These results indicate that all the animals in this group were sterilely protected. Similarly, the groups given the high dose of Ad5-CI-pIFN-γ or the combination of Ad5-CI-pIFN-α and the high dose of Ad5-CI-pIFN-γ were also sterilely protected. Surprisingly, we were not able to detect antiviral activity or pIFN-α or pIFN-γ protein in the plasma of the animals in any of the protected groups. Previously, we had demonstrated a correlation between the level of antiviral activity, pIFN-α protein, and protection when we administered a 10-fold-higher dose of Ad5-pIFN-α (Chinsangaram et al. 2003, supra; Grubman, M. J. 2005. *Biologicals* 33: 227-234; Moraes et al., 2003, supra).

As an initial approach to determine the mechanism of protection induced by this treatment regimen, we examined gene expression in PBMCs. Unfortunately, limited by the large number of samples, we did not include the group inoculated with the combination of Ad5-CI-pIFN-α and the low dose of Ad5-CI-pIFN-γ. Nevertheless, consistent with the results that we obtained by cell culture, we did detect the induction of mRNAs for two IFN-γ-stimulated genes, the INDO and IP-10 genes, in the two protected groups that we examined, i.e., the group given the high dose of Ad5-CI-pIFN-γ alone and the group given the combination of Ad5-CI-pIFN-α and the high dose of Ad5-CI-pIFN-γ, but not in the unprotected groups, i.e., the control group and the group given Ad5-CI-pIFN-α alone. Furthermore, there was a synergistic increase in the expression of these two genes at 1 to 3 days postadministration in the group given the combination of Ad5-CI-pIFN-α and the high dose of Ad5-CI-pIFN-γ. The induction of these genes was statistically significant ($P<0.05$) compared to the levels of expression obtained for the control and Ad5-CI-pIFN-α groups. There was also somewhat more than an additive increase in OAS mRNA in this group.

While our limited examination of gene expression cannot definitively explain the mechanism of protection afforded by the combination IFN treatment or the high-dose-IFN-γ treatment, it does identify some candidate genes or gene classes that may be involved. For example, IP-10 is a chemokine that is involved in the recruitment of T cells (Bonecchi et al., 1998. *J. Exp. Med.* 187: 129-134; Dufour et al. *J. Immunol.* 168: 3195-3204) and NK cells to sites of infection (Arai et al. 2002. *Cell. Immunol.* 219: 48-56; Kakimi et al. 2001. *J. Exp. Med.* 194: 163-172; Loetscher et al. 1996. *J. Exp. Med.* 184: 963-969; Taub et al., 1995. *J. Immunol.* 155: 3877-3888; Trifilo et al. 2004. *J. Virol.* 78: 585-594). NK cells are involved in the rapid, innate response to a variety of pathogens, including viruses. These cells predominate in the peripheral blood and spleen but can be induced to traffic to other compartments during infection (Salazar-Mather and Hokeness. 2006. *Current Topics in Microbiology and Immunology* 303: 29-46). Thus, the induction of IP-10 by IFN-γ treatment and its synergistic induction by the combined treatment suggest that the presence of this gene product at the time of infection may allow the very rapid recruitment of cells that have an essential role in viral clearance. Additional chemokines are induced by both type I and II IFNs (Hokeness et al. 2005. *J. Immunol.* 174: 1549-1556; Salazar-Mather et al.

2003. *Viral Immunol.* 16: 291-306) and are also involved in the trafficking of NK cells as well as macrophages to sites of viral infection (Salazar-Mather et al., 2003, supra) and possibly in modulating NK cell-mediated cytolytic responses (Taub et al., supra). The possible role that these or other chemokines may play in the IFN-α/γ-induced protection against FMDV needs to be examined.

The second gene that was synergistically induced by the combination IFN treatment is the INDO gene, which encodes an enzyme involved in the tryptophan degradation pathway. It has been demonstrated that the antiviral activity of IFN-γ against a number of viruses, including human CMV (Bodaghi et al., supra), herpes simplex virus type I (Adams et al., supra), and measles virus (Obojes et al., supra), correlates with the induction of INDO.

Other studies have demonstrated that IFN-γ has antiviral activity against another member of the picornavirus family, i.e., coxsackievirus (Henke et al. 2001; Henke et al. 2003; Horwitz et al., supra), and that there is a correlation with the IFN-γ-induced protection and induction of iNOS (Henke et al. 2003, supra). Our results indicate that iNOS mRNA is only minimally induced in treated cells compared to the induction of INDO and IP-10 mRNAs and not induced in swine treated with type I or II IFNs.

Clearly, type I and II IFNs induce many genes that either have direct antiviral activity or indirectly induce the activation of a variety of antiviral pathways. The information obtained in this study suggests that genes having both types of activity are upregulated by the combination IFN treatment and may cooperatively control FMDV infection. Utilizing a comprehensive understanding of the multiple host pathways that can be induced to rapidly control FMDV infection, we can develop more-effective disease control strategies, including the administration of antivirals in combination with our Ad5-FMD marker vaccine.

Production and manipulation of the isolated polynucleotide molecules described herein are within the skill in the art and can be carried out according to recombinant techniques described, among other places, in Sambrook et al., 1989. *Molecular Cloning: A Laboratory Manual,* 2d ed., Cold Spring Harbor Laboratory Press, Cold Spring Harbor, N.Y. and Innis et al. (eds). 1995. *PCR Strategies,* Academic Press, Inc., San Diego, which are incorporated herein by reference.

The subject invention provides vectors comprising isolated polynucleotide molecules comprising genetically modified nucleic acid sequences that encode porcine IFNα and porcine IFNγ.

The subject invention provides a vector comprising a genetically modified nucleic acid sequence that encodes a genetically modified infectious RNA molecule that encodes a genetically modified Foot and Mouth Disease Virus.

For purposes of the present invention, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization,* Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990.

*Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of the IFNα and IFNγ of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, IFNα and IFNγ activity as described herein. Such variants may result from, for example, genetic polymorphism or from human manipulation. Biologically active variants of the IFNα and IFNγ of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired IFNα and IFNγ activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of IFNα and IFNγ can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "FMD" encompasses disease symptoms in swine, cows, sheep, and goats caused by a FMDV infection. Examples of such symptoms include, but are not limited to: fever, lameness and vesicular lesions on the feet, tongue, snout and teats.

The terms "foot and mouth disease virus" and "FMDV", as used herein, unless otherwise indicated, mean any strain of FMD viruses.

The term "open reading frame", or "ORF", as used herein, means the minimal nucleotide sequence required to encode a particular FMDV protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine, bovine, caprine, and ovine cells.

A "functional virion" is a virus particle that is able to enter a cell capable of hosting a FMDV, and express genes of its particular RNA genome (either an unmodified genome or a genetically modified genome as described herein) within the cell. Cells capable of hosting a FMDV include, for example, baby hamster kidney cells (e.g., BHK-21 cells) and swine kidney cells (e.g., IBRS-2 cells). Other cells may also serve as suitable host cells for FMD virions.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polypeptide sequences, optionally comprising non-protein groups such as carbohydrate moieties and/or lipid moieties.

In a further preferred embodiment, an antigenic epitope of the genetically modified FMDV of the present invention is a detectable antigenic epitope. Such isolated polynucleotide molecules and the FMD viruses they encode are useful, inter alia, for studying FMDV infections in cows, swine, goats, and sheep, determining successfully vaccinated cows, swine, goats, and sheep, and/or for distinguishing said vaccinated animals from cows, swine, goats, and sheep infected by a wild-type FMDV. Preferably, such isolated polynucleotide molecules further contain one or more mutations that genetically disable the encoded FMDV in its ability to produce FMD, and more preferably are able to elicit an effective immunoprotective response in a porcine animal against infection by a FMDV.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention comprise vectors comprising genes encoding pIFNγ or a combination of pIFNα and pIFNγ. Adjuvants can be used in the vaccine of the present invention and can include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

The effective dose amount of virus, infectious RNA molecule, plasmid, or viral vector, of the present invention can be determined, using known techniques, taking into account factors that can be determined by one of ordinary skill in the art such as the weight of the animal to be vaccinated.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Human 293 cells were used to generate and grow recombinant Ad5 viruses and to determine virus titer (Graham et al., Moraes et al. 2002, supra). Baby hamster kidney cells (BHK-21, clone 13) were used to measure FMDV titers in plaque assays. IBRS-2 (swine kidney) cells were used to measure antiviral activity in plasma from inoculated animals by a plaque-reduction assay (Chinsangaram et al. 2001, supra). The recombinant viruses Ad5-CI-pIFN-α, Ad5-CI-pIFN-β, and Ad5-CI-pIFN-γ were constructed as described below, while Ad5-VSV glycoprotein (Ad5-VSVG) was described previously (Moraes et al., 2001, supra). FMDV serotype A24 (strain Cruzeiro, Brazil, 1955, provided by A. Tanuri, University of Rio de Janeiro) was isolated from vesicular lesions of an infected bovine. The 50% pig infectious dose ($PID_{50}$) was determined by standard protocols (Burrows, supra).

Example 2

Ad5 Construction and Expression of pIFN-α, β, and γ Proteins

To optimize expression of recombinant proteins, we genetically engineered new Ad5 vectors. pAd5-Blue, which contains the cytomegalovirus (CMV) promoter/enhancer for control of foreign gene expression and a functional LacZ gene fragment (Moraes et al. 2001, supra) was digested with ClaI and XbaI to remove the Amp and LacZ genes and the *Renilla* luciferase gene (pRL-TK; Promega, Madison, Wis.) was inserted, creating pAd5-RL. A unique BstBI site was added directly upstream of the CMV promoter/enhancer of pAd5-RL by site-directed mutagenesis, and this vector was then digested with BstBI/ClaI to remove the CMV promoter/enhancer region. The CMV promoter/enhancer, intron, and T7 promoter region from the vector pCI (Promega) was PCR amplified with primers containing BstBI and ClaI sites at their 5' and 3' ends, respectively, and inserted into BstBI- and ClaI-digested pAd5-RL to form pAd5-CI-RL. The bovine growth hormone poly(A) signal from pcDNA3 (Invitrogen, Carlsbad, Calif.) was PCR amplified with a forward primer containing an XbaI site and a reverse primer containing an NheI site and subsequently cloned into the XbaI site of pAd5-CI-RL to form pAd5-CI-RL-BGH. This vector expressed higher levels of luciferase than our original Ad5 vector containing the CMV promoter/enhancer (unpublished data). To construct Ad5-CI vectors containing IFN-α and -β genes, pAd5-pIFN-α and pAd5-pIFN-β were digested with ClaI and XbaI and the IFN coding regions were cloned into ClaI- and XbaI-digested pAd5-CI-RL-BGH, resulting in pAd5-CI-pIFN-α and pAd5-CI-pIFN-β, respectively. PacI-linearized plasmids were transfected into 293 cells to generate Ad5-CI-pIFN-α and Ad5-CI-pIFN-β as previously described (Moraes et al. 2001, supra).

The pIFN-γ gene was obtained by PCR amplification of cDNA derived from RNA extracted from concanavalin A-treated porcine lymphocytes using a forward primer containing a ClaI site (in bold), CTAGCGATCGATGAGTTATACAACTTATTTCTTAGCT TTTC (SEQ ID NO:1), and a reverse primer containing a XbaI site (in bold), TGCAGTCTAGATTATTTT GATCTCTCTGCCCTTGGAACATA (SEQ ID NO:2). The amplified PCR product was sequenced and cloned into pAd5-CI-RL-BGH as described above.

IBRS-2 cells were infected with Ad5-CIpIFNα or Ad5-CI-pIFNβ at a multiplicity of infection (MOI) of 20, and 24 h. postinfection (p.i.), the supernatants were removed, centrifuged through a Centricon 100 filter at 2000 rpm for 10 min, and acid treated as previously described (Wu et al., supra). A similar procedure was used for pIFN-γ, but the supernatant of infected IBRS-2 cells was not acid-treated since IFN-γ is acid sensitive.

The expression of each cytokine was verified by infection of IBRS-2 cells (Table 1). Real-time reverse transcription-PCR indicated that pIFN-α mRNA was expressed at 10- to 12-fold-lower levels than pIFN-γ mRNA, yet the level of pIFN-α protein detected in supernatants was 160- to 440-fold higher than the level of pIFN-γ.

TABLE 1

Expression of porcine IFNα and porcine IFNγ in IBRS-2 cells infected with recombinant Ad5s.

| Recombinant Ad5[a] | Time p.i.(hr) | mRNA (fold induction)/SD[b] α | mRNA (fold induction)/SD[b] γ | Protein conc. (pg/ml)/SD[c] α | Protein conc. (pg/ml)/SD[c] γ | Antiviral activity (units/ml)[d] |
|---|---|---|---|---|---|---|
| Ad5-Blue | 24 | $0.4 \pm 0.1^{e}$ | $0.5 \pm 0.2^{f}$ | <20.0 | <15.0 | <2 |
|  | 48 | $0.1 \pm 0.2^{e}$ | $0.6 \pm 0.1^{f}$ | <20.0 | <15.0 | <2 |
| Ad5-pIFNα + Ad5-Blue | 24 | $1.2 \times 10^4 \pm 6.3 \times 10^2$ | $0.6 \pm 0.6$ | $8.7 \times 10^6 \pm 2.0 \times 10^6$ | <15.0 | $3.2 \times 10^5$ |
|  | 48 | $8.5 \times 10^3 \pm 2.0 \times 10^3$ | $0.4 \pm 0.0$ | $1.1 \times 10^7 \pm 1.4 \times 10^6$ | <15.0 | $3.2 \times 10^5$ |
| Ad5-pIFNγ + Ad5-Blue | 24 | $0.3 \pm 0.1$ | $1.7 \times 10^5 \pm 5.4 \times 10^4$ | <20.0 | $5.2 \times 10^4 \pm 4.7 \times 10^3$ | $8.0 \times 10^2$ |
|  | 48 | $0.5 \pm 0.0$ | $1.0 \times 10^5 \pm 9.8 \times 10^2$ | <20.0 | $2.5 \times 10^4 \pm 3.1 \times 10^2$ | $4.0 \times 10^2$ |
| Ad5-pIFNα + Ad5-pIFNγ | 24 | $8.0 \times 10^3 \pm 7.5 \times 10^2$ | $2.6 \times 10^5 \pm 8.8 \times 10^4$ | $7.3 \times 10^6 \pm 4.5 \times 10^4$ | $2.2 \times 10^4 \pm 1.2 \times 10^3$ | $3.2 \times 10^5$ |
|  | 48 | $1.3 \times 10^3 \pm 3.0 \times 10^2$ | $1.1 \times 10^5 \pm 7.9 \times 10^3$ | $1.1 \times 10^7 \pm 3.3 \times 10^6$ | $1.5 \times 10^4 \pm 4.0 \times 10^2$ | $3.2 \times 10^5$ |

[a]IBRS-2 cells were infected at an MOI of 20 with the same amount of the indicated Ad5.
[b]Compared to value for Ad5-Blue infected cells; except as noted SD = standard deviation.
[c]Determined by ELISA; SD = standard deviation
[d]Dilution that results in a 50% reduction in the number of plaques
[e]Compared to value for mock infected cells.

Example 3

Antiviral Effect of pIFN-γ

The biological activity of IFN-γ was determined by a plaque reduction assay in IBRS-2 cells (Chinsangaram et al., 2003, supra). Briefly, IBRS-2 cells were incubated with dilutions of supernatants containing pIFN-α, pIFN-β, or pIFN-γ or combinations of two IFNs. After 24 h, supernatants were removed, and the cells were infected for 1 h with approximately 100 PFU of FMDV serotype A12 and overlaid with gum tragacanth. Plaques were visualized 24 h later by being stained with crystal violet (Chinsangaram et al. 2001, 2003, supra). Antiviral activity was reported as the reciprocal of the highest supernatant dilution that resulted in a 50% reduction in the number of plaques relative to the number of plaques in untreated infected cells. Serial dilutions of plasma samples, starting at a 1:25, were incubated with IBRS-2 cells for 24 h, and the cells were subsequently infected and treated as described above. To neutralize the antiviral activity, pIFN-α monoclonal antibody (MAb) F17 (PBL Biomedical Laboratories, Piscataway, N.J.) and pIFN-γ MAb P2C11 (Pierce Endogen, Rockford, Ill.) were used.

As shown in Table 1, IFN-γ as well as IFN-α has antiviral activity against FMDV.

The effects of IFN-α and IFN-γ, as well as pIFN-β, on the FMDV yield in an overnight infection was determined. IBRS-2 cells were incubated overnight with dilutions of IFN-containing supernatants. Supernatants were removed and cells washed with minimal essential medium (MEM; Gibco BRL/Invitrogen). Cells were infected at an MOI of 1 with FMDV A12 for 1 h, and unabsorbed virus was inactivated by washing the cells with 150 mM NaCl, 20 mM morpholineethanesulfonic acid (MES) (pH 6). MEM was added, and incubation continued for 24 h. Virus was released by one freeze-thaw cycle. As a control, infected cells were frozen and thawed at 1 h p.i. Virus yields were determined by plaque assay on BHK-21 cells and expressed by subtracting the titers of virus in cells infected for 1 h from the 24-h titers.

Approximately 10 to 100 units of either IFN-α or IFN-β can reduce the virus yield between 5,000- and 60,000-fold, while an equivalent amount of IFN-γ reduces the virus yield by 2,000- to 5,000-fold (data not shown). Higher concentrations of IFN-α or IFN-β had little or no additional effect.

Example 4

Synergistic Effect of Type I and Type II IFNs

To determine if a combination of IFN-α and IFN-γ had an enhanced antiviral effect compared to that of the individual IFNs, approximately 1 unit of IFN-α or IFN-γ was titrated with various amounts of the other IFNs and analyzed by a plaque reduction assay (see Experiment 3) on IBRS-2 cells. As shown in Table 2, 1 unit of IFN-α alone reduced the number of plaques by 50%, and this antiviral effect was significantly enhanced when combined with amounts of IFN-γ as low as 0.062 unit. The effect was not as dramatic when the reciprocal experiment was performed. The level of inhibition was not a result of doubling the total amount of IFN, since the addition of either 2 units of IFN-α or IFN-γ individually did not achieve a comparable degree of inhibition (Table 2). Similar results were obtained when 1 unit of pIFN-β was titrated with various amounts of pIFN-γ (data not shown). The specificity of the IFN effect was demonstrated by the addition of neutralizing MAbs against either pIFN-α or pIFN-γ. Each antibody partially abolished the antiviral activity of the IFN combination, while pretreatment with both MAbs completely inhibited the antiviral activity (FIG. 1).

TABLE 2 pIFN-α and pIFN-γ synergistically inhibit FMDV plaque formation.

| pIFN-α (U/ml)[a] | pIFN-γ (U/ml)[a] | Mean number of plaques ± SD[b] | Fold Reduction |
|---|---|---|---|
| 0 | 0 | $143 \pm 24.2$ |  |
| 2 | 0 | $19 \pm 23.3^{d}$ | 7.5 |
| 1 | 0 | $71 \pm 16.9$ | 2.0 |
| 1 | 0.031 | $74 \pm 17.0$ | 1.9 |
| 1 | 0.062 | $59 \pm 25.0$ | 2.4 |
| 1 | 0.125 | $35 \pm 28.1$ | 4.1 |
| 1 | 0.25 | $17 \pm 13.4$ | 8.4 |
| 1 | 0.50 | $7 \pm 8.8$ | 20.4 |
| 1 | 1.00 | $2 \pm 2.4$ | 71.5 |
| 0 | 2 | $85 \pm 2.1^{d}$ | 1.6 |

TABLE 2-continued pIFN-α and pIFN-γ synergistically inhibit FMDV plaque formation.

| pIFN-α (U/ml)[a] | pIFN-γ (U/ml)[a] | Mean number of plaques ± SD[b] | Fold Reduction |
|---|---|---|---|
| 0 | 1 | 100 ± 5.1 | 1.4 |
| 0.031 | 1 | 99 ± 6.9 | 1.4 |
| 0.062 | 1 | 95 ± 3.1 | 1.5 |
| 0.125 | 1 | 97 ± 12.0 | 1.5 |
| 0.25 | 1 | 66 ± 12.2 | 2.2 |
| 0.50 | 1 | 30 ± 12.3 | 4.8 |
| 1 | 1.00 | 2 ± 2.4 | 71.5 |

[a]IFNs were obtained from supernatants of IBRS-2 cells infected with Ad5s as described in Experiment 2 and incubated with IBRS-2 cells for approximately 24 h.
[b]After treatment with IFNs, IBRS-2 cells were infected with approximately 100 plaques of FMDV for 1 h, overlaid with gum tragacanth, and incubated for approximately 24 h. Results are means from four repetitions unless otherwise noted.
[c]The reductions (n-fold) was calculated by dividing the number of plaques in untreated cells by the number of plaques in treated cells.
[d]Results are means from two repetitions.

Figure 2:
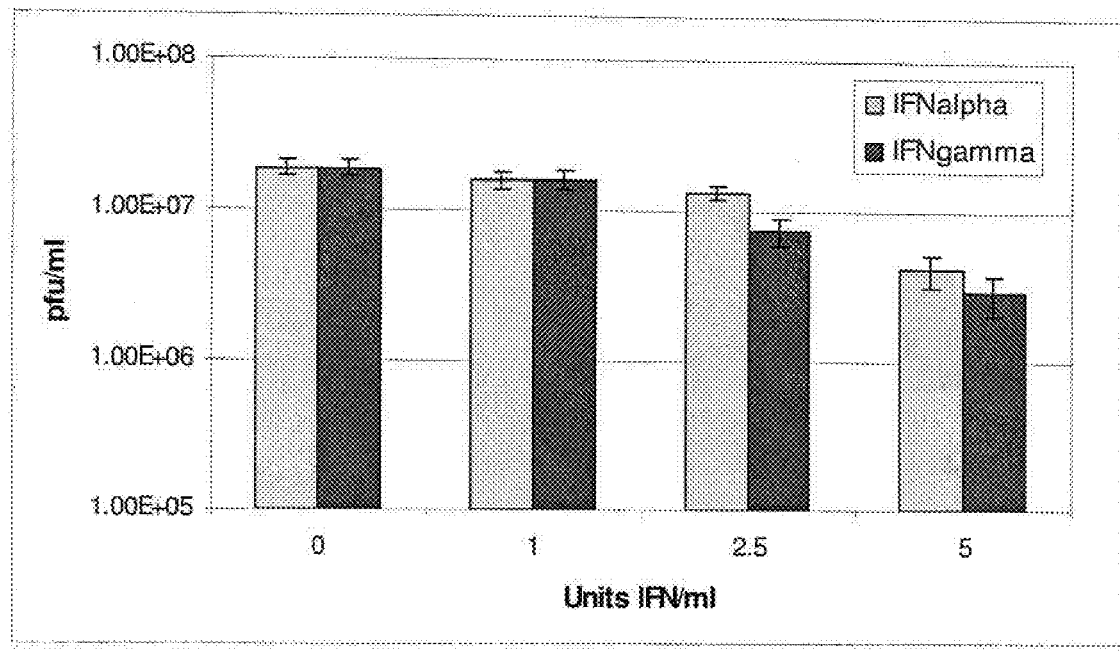
FIGS. 2A and 2B show the effect of pIFN-α and pIFN-γ on yield of FMDV A12 in IBRS-2 cells.
Figure 2:
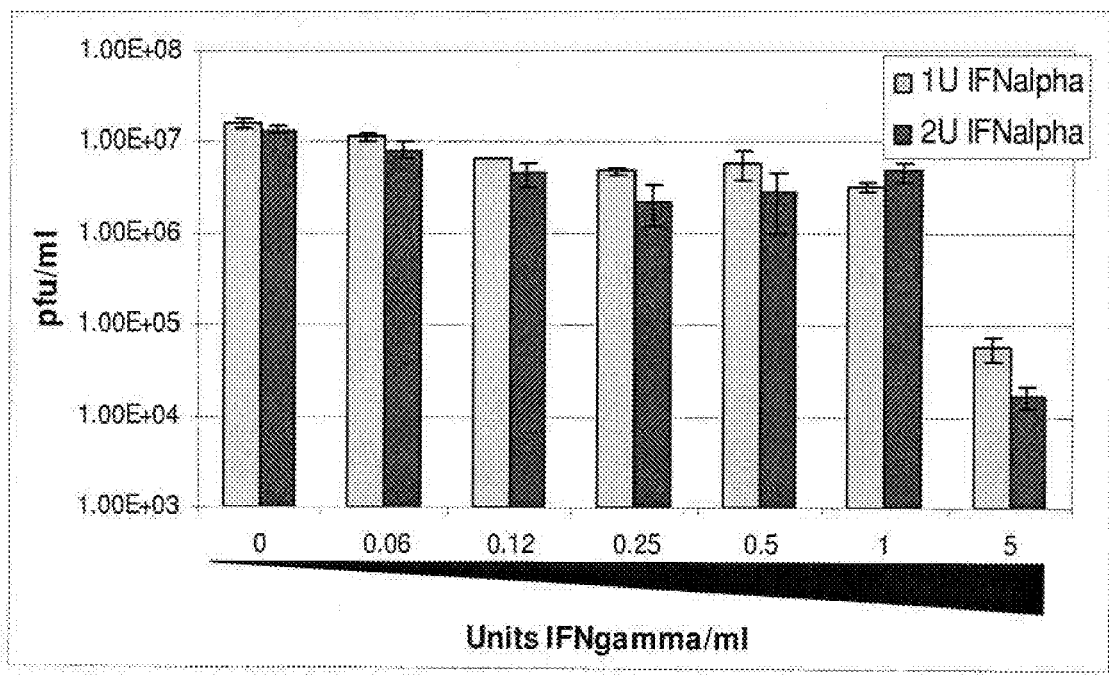

We also examined the effect of a combination of 1 or 2 units of IFN-α and various amounts of IFN-γ on FMDV yield after a 24-h infection (FIG. 2). The combination of 2 units of IFN-α and 5 units of IFN-γ reduced the virus yield by approximately 171-fold compared to the yield of either pretreatment alone.

Example 5

Genes Induced by pIFN-α, p IFN-γ, or a Combination in Swine Cells

Since the swine genome has not yet been completely sequenced, in our initial attempt to understand the basis for the synergistic antiviral effect of the combined IFNs, we examined a set of genes which are known to be induced by each IFN and for which sequences are available (Table 3).

TABLE 3

Oligonucleotide primer and probe sequences for amplification of pIFNs and ISGs used in real-time reverse transcription-PCR.

| Gene | Primer[a] | Sequence 5' to 3' | Final conc. (nM) | SEQ ID NO: | GenBank Accession No. |
|---|---|---|---|---|---|
| GAPDH | GAPDH-327F | CGTCCCTGAGACACGATGGT | 100 | 3 | AF017079 |
|  | GAPDH-380R | CCCGATGCGGCCAAAT | 100 | 4 |  |
|  | GAPDH-348T | AAGGTCGGAGTGAACG | 200 | 5 |  |
| 18S rRNA | rRNA-178F | GCATTCGTATTGCGCCG | 50 | 6 | AF102857 |
|  | rRNA-228R | CCGTCTTGCGCCGGT | 50 | 7 |  |
|  | rRNA-196V | CAAGAATTTCACCTCTA | 200 | 8 |  |
| Mx1 | Mx1-803F | GAGGTGGACCCCGAAGGA | 100 | 9 | M65087 |
|  | Mx1-859R | CACCAGATCCGGCTTCGT | 100 | 10 |  |
|  | Mx1-824T | AGGACCATCGGGATC | 200 | 11 |  |
| OAS | OAS-889F | CTGTCGTTGGACGATGTATGCT | 100 | 12 | AJ225090 |
|  | OAS-954R | CAGCCGGGTCCAGAATCA | 100 | 13 |  |
|  | OAS-919T | TCAAGAAACCCAGGCCT | 200 | 14 |  |
| PKR | PKR-968F | TGGTGCATGAGATGCTCCA | 100 | 15 | AB104654 |
|  | PKR-1048R | CCAAATCCACCTGAGCCAATT | 100 | 16 |  |
|  | PkR-994T | CCAGGTTTGTCGAAGAT | 200 | 17 |  |
| IFNα | IFN-α-236F | TGGTGCATGAGATGCTCCA | 100 | 18 | M28623 |
|  | IFN-α-290R | GCCGAGCCCTCTGTGCT | 100 | 19 |  |
|  | IFN-α-2256T | CAGACCTTCCAAGCTCT | 200 | 20 |  |
| IFNβ | IFN-β-11F | AAGTGCATCCTCCAAATCGCT | 100 | 21 | M86762 |
|  | IFN-β-69R | GCTCATGGAAAGAGCTGTGG | 100 | 22 |  |
|  | IFN-β-32T | TCCTGATGTGTTCTC | 200 | 23 |  |
| RANTES | RANTES-54F | TGGCAGCAGTCGTCTTTATCA | 300 | 24 | F14636 |
|  | RANTES-125R | CCCGCACCCATTTCTTCTC | 900 | 25 |  |
|  | RANTES-101T | TGGCACACACCTGGCGGTTCTTTC | 200 | 26 |  |
| IFNγ | IFN-γ 318F | TGGTAGCTCTGGGAAACTGAATG | 300 | 27 | NM213948 |
|  | IFN-γ 396R | GGCTTTGCGCTGGATCTG | 300 | 28 |  |
|  | IFN-γ 342T | CTTCGAAAAGCTGATTAAAATTCCGGTAGATAATCTGC | 200 | 29 |  |
| iNOS | iNOS-58F | CGTTATGCCACCAACAATGG | 300 | 30 | U59390 |
|  | iNOS-58F | AGACCCGGAAGTCGTGCTT | 300 | 31 |  |
|  | iNOS-58F | ATCAGGTCGGCCATCACCGTG | 200 | 32 |  |
| INDO | INDO 144F | CTGGTTTCGCTATTGGTGGAA | 300 | 33 | CJ011949 |
|  | INDO 235R | GCATCCAGGTCTTCACACTGTATT | 300 | 34 |  |
|  | INDO 178T | CTGCAATCAAGGTGATCCCCACTCTATTCA | 150 | 35 |  |

TABLE 3-continued

Oligonucleotide primer and probe sequences for amplification of pIFNs and ISGs used in real-time reverse transcription-PCR.

| Gene | Primer[a] | Sequence 5' to 3' | Final conc. (nM) | SEQ ID NO: | GenBank Accession No. |
|---|---|---|---|---|---|
| IRF1 | IRF1-55F | AATCCAGCCCTGATACCTTCTCT | 900 | 36 | AJ583706 |
| | IRF1-167R | GGCCTGTTCAATGTCCAAGTC | 900 | 37 | |
| | IRF1-100T | TGCCTGATGACCACAGCAGCTACACA | 150 | 38 | |
| IP-10 | CXCL10-174F | TTGAAATGATTCCTGCAAGTCAA | 900 | 39 | NM_00100861 |
| | CXCL10-254R | GACATCTTTTCTCCCCATTCTTTT | 900 | 40 | |
| | CXCL10-198T | CTTGCCCACATGTTGAGATCATTGCCAC | 200 | 41 | |

[a]F, forward primer; R, reverse primer; T, TaqMan 6-carboxyfluorescein-MGB probe; V, TaqMan VIC-MGB probe.

Expression of IFN-stimulated genes was analyzed in cultured IBRS-2 cells or purified peripheral blood mononuclear cells (PBMCs) isolated from experimentally vaccinated animals. IBRS-2 cells were directly infected with Ad5-Blue (MOI=20), Ad5-CI-pIFN-α (MOI=10) and Ad5-Blue (MOI=10), Ad5-CI-pIFN-γ (MOI=10) and Ad5-Blue (MOI=10), or Ad5-CI-pIFN-α (MOI=10) and Ad5-CI-pIFN-γ (MOI=10) for 24 h. Alternatively, monolayers of IBRS-2 cells were incubated for 24 h with pretreated supernatants derived from similar cells infected with the above-mentioned Ad5s and containing 100 units of pIFN-α, 100 units of pIFN-γ, or 100 units each of pIFN-α and pIFN-γ. PBMCs were purified from heparinized blood using Lymphoprep (Axis-Shield, Oslo, Norway). RNA was extracted from approximately $10^7$ cells (IBRS-2 cells or PBMCS) by utilizing an RNeasy miniprep kit (QIAGEN, Valencia, Calif.), and a quantitative real-time reverse transcription-PCR was used to evaluate the mRNA levels of several ISGs. Approximately 1 μg of RNA was treated with DNase I (Sigma, St. Louis, Mo.) and was used to synthesize cDNA with Moloney murine leukemia virus reverse transcriptase (Invitrogen) and random hexamers according to the manufacturer's directions. An aliquot (1/40) of the cDNA was used as the template for a real-time PCR using TaqMan universal PCR master mix (Applied Biosystems, Foster City, Calif.). Primers and TaqMan minor-groove binding (MGB) were designed with Primer Express software v.1.5 (Applied Biosystems) or obtained from the PIN database (http://ars.usda.gov/Services/docs.htm?docid=6065). 18S rRNA or porcine glyceraldehyde-3-phosphate dehydrogenase (GAPDH) was used as the internal control to normalize the values for each sample. The sequences of primers and probes that were used are listed in Table 3. Reactions were performed in an ABI Prism 7000 sequence detection system (Applied Biosystems). Relative mRNA levels were determined by comparative cycle threshold analysis (user bulletin 2; Applied Biosystems) utilizing as a reference the samples at 0 dpc for the animal experiment or the mock-treated samples for the cultured IBRS-2 cells. For statistical analysis, Student's t test was performed using Microsoft Excel.

As has been previously shown, three genes known to be induced by IFN-α, the OAS, Mx1, and PKR genes, had enhanced levels of mRNA after the treatment of cells with this cytokine (Chinsangaram et al. 2001, supra; de los Santos et al., supra) (Table 4). There was also a significant induction of INDO, the 10-kDa IFN-γ-inducible protein (IP-10; also referred to as CXCL10 in GenBank), and RANTES (regulated on activation, normal T-cell expressed and secreted). Similarly, treatment with IFN-γ significantly enhanced the levels of INDO, iNOS, and IP-1; three genes known to be induced by IFN-γ, as well as the levels of IFN-β, IFN-regulatory factor 1 (IRF1), Mx1, OAS, and RANTES. In the combined treatment, the level of OAS was enhanced by about 40% compared to its levels after the individual treatments, while the level of Mx1 was decreased by about 20%, IRF1 by about 45%, and IFN-β by threefold.

In a similar experiment, we infected IBRS-2 cells with Ad5-pIFN-α, Ad5-pIFN-γ, the combination Ad5-pIFN-α and Ad5-pIFN-γ, and a control Ad5. The infection was stopped at 24 or 48 h p.i., RNA was extracted, and real-time reverse transcription-PCR was performed. Table 4 shows that after Ad5 infections, there was an induction of the same genes that responded to the treatment with individual IFN proteins. The combined treatment, however, resulted in a synergistic increase in the expression of two IFN-γ-inducible genes, INDO and IP-10 (by two- to fourfold), and a synergistic increase (two- to threefold) in OAS and Mx1 at 48 h p.i. Similar results were obtained when the two experiments described above were repeated.

Example 6

Clinical Effects of Ad5-CI-pIFN-Containing Viruses

The antiviral effects of the combined IFNs were examined in swine to determine their effectiveness in inducing a synergistic antiviral and rapid protective response in animals. The animal experiment was performed in the secure disease agent isolation facilities at the Plum Island Animal Disease Center according to a protocol approved by the Institutional Animal Care and Use Committee. In this experiment, 18 Yorkshire gilts (approximately 35 to 40 lb) were divided into six groups containing three animals per group and each group was housed in a separate room. All animals were inoculated intramuscularly with 2 ml of the various Ad5s as indicated in Table 5, and each animal received a total of $10^{10}$ PFU of Ad5. The animals were monitored clinically for adverse effects from Ad5-CI-pIFN-α and Ad5-CI-pIFN-γ administration, including fever and lethargy, and plasma was obtained daily to assay for antiviral activity and the presence of pIFN-α and pIFN-γ by enzyme-linked immunosorbent assay (ELISA) (see below). All animals in the above-described groups were challenged 1 day p.i. with $10^5$ PFU of FMDV serotype A24, i.e., 13 50% pig infectious doses, at two sites in the heel bulb of the left rear foot (Doel et al., Sa-Carvalho et al., supra). This route of challenge in swine is one recommended by the OIE (OIE Biological Standard Commission, supra) and has Groups of three swine were inoculated intramuscularly with the various Ad5 viruses, and all animals received a combined dose of $10^{10}$ PFU by the addition of the control Ad5-VSVG virus when required. A control group (group 1) received Ad5-VSVG, group 2 received $10^8$ PFU of Ad5-pIFN-α/animal, group 3 received $10^9$ PFU of Ad5-CI-pIFN-γ, group 4 received $10^{10}$ PFU of Ad5-CI-pIFN-γ, group 5 received $10^8$ PFU of Ad5-pIFN-α plus $10^9$ PFU of Ad5-CI-pIFN-γ, and group 6 received $10^8$ PFU of Ad5-pIFN-α plus $10^{10}$ PFU Ad5-CI-pIFN-γ. Animals were challenged 1 day postinoculation.

A slightly modified double-capture ELISA previously developed in our lab was used for the quantitation of IFN-α

TABLE 4

Induction of IFN-stimulated Genes by p IFNα, p IFNγ, and the combination.

| Treatment[a] | Time | Fold Induction[c] IFNα | IFNβ | IFNγ | INDO | iNOS | IP-10 | IRF1 | Mx1 | OAS | PKR | RANTES |
|---|---|---|---|---|---|---|---|---|---|---|---|---|
| IFNα | 24 h | 1.4 | 10.7 | 1.1 | 61.2 | 1.5 | 778.7 | 5 | 109.9 | 22267.6 | 6.4 | 15.0 |
| IFNγ | 24 h | 1.2 | 32.7 | 2.0 | 2646.7 | 18.4 | 5732.7 | 28.1 | 39.3 | 2957.2 | 3.2 | 22.4 |
| IFNα + IFNγ | 24 h | 1.0 | 12.9 | 1.0 | 2846.6 | 20.3 | 5614.7 | 16.2 | 79.3 | 35857.8 | 6.5 | 22.7 |
| Ad5-Blue | 24 h | 1.7 | 2.3 | 2.6 | 1.1 | 6.78 | 1.3 | 1.1 | 0.7 | 0.9 | 2.0 | 1.3 |
| Ad5-IFNα | 24 h | 8220.4 | 0.4 | 13.5 | 26.8 | 3.8 | 311.9 | 7.0 | 157.6 | 6960.6 | 6.7 | 40.8 |
| Ad5-IFNγ | 24 h | 0.6 | 0.2 | 225849.2 | 415.9 | 18.6 | 1332.6 | 19.2 | 10.6 | 29.9 | 3.3 | 16.2 |
| Ad5-IFNα + Ad5-IFNγ | 24 h | 3875.1 | 0.5 | 142935.0 | 762.7 | 9.7 | 4513.4 | 22.2 | 185.5 | 7804.0 | 6.7 | 70.0 |
| Ad5-Blue | 48 h | 0.1 | 0.0 | 0.0 | 0.0 | 0.3 | 0.2 | 0.4 | 0.8 | 0.2 | 0.5 | 1.9 |
| Ad5-IFNα | 48 h | 2120.2 | 0.1 | 0.0 | 18.2 | 1.2 | 654.8 | 3.5 | 207.9 | 6122.9 | 6.4 | 59.1 |
| Ad5-IFNγ | 48 h | 0.2 | 0.2 | 103194.0 | 736.7 | 14.1 | 11706.3 | 19.6 | 32.1 | 82.4 | 3.1 | 63.1 |
| Ad5-IFNα + Ad5-IFNγ | 48 h | 541.2 | 1.2 | 142935.0 | 2288.2 | 6.0 | 49667.0 | 23.4 | 407.3 | 19215.7 | 8.1 | 128.9 |

[a]IBRS-2 cells were incubated with 100 units of the indicted IFNs for 24 hrs and total RNA extracted.

been used previously by us and many other investigators (Caron et al., Cedillo-Barron et al., Chinsangaram et al. 2003, Liao et al., Sanz-Parra et al., Wang et al., supra). The animals were monitored for 3 weeks after challenge. Rectal temperatures, lesion data, and the physical conditions of the animals were determined daily. Blood and nasal swab specimens were collected daily for the first 7 days after challenge, and serum samples were collected weekly. Lesion scores of the animals were determined at 14 days postchallenge (dpc) by determining the number of digits with lesions and adding the snout and tongue combined, if vesicles were present (maximum score, 17).

The dose of Ad5-CI-pIFN-α used was $10^8$ PFU/animal based on previous animal experiments in which we found that swine inoculated with this dose of a similar vector expressed low levels of IFN-α but were not completely protected from direct FMDV challenge, while swine inoculated with $10^9$ PFU/animal produced significantly higher levels of biologically active IFN-α and were sterilely protected when challenged 1 to 3 days later (Chinsangaram et al. 2003, supra; Grubman and Baxt, supra). Since we found that Ad5-CI-pIFN-γ expressed significantly lower levels of recombinant protein than Ad5-CI-pIFN-α in infected IBRS-2 cells (Table 1), in the current study, we used $10^9$ and $10^{10}$ PFU of Ad5-CI-pIFN-γ/animal.

Utilizing this information, we inoculated groups of swine with presumably nonprotective doses of Ad5-CI-pIFN-α or Ad5-CI-pIFN-γ alone or combinations of the two (Table 5).

(Wu et al., supra). Nonfat dry milk (5%) in phosphate-buffered saline (PBS) containing 0.05% Tween 20 (PBST) was used instead of 5% goat serum in PBST as the blocking buffer. The pIFN-α concentrations were calculated by linear regression analysis of a standard curve generated with recombinant pIFN-α (PBL Biomedical Laboratories). A standard antigen capture ELISA was performed as previously described (Bautista et al., supra) for the quantitation of IFN-γ. Briefly, anti-pIFN-γ MAb P2G10 was used as the capture antibody (BD Pharmingen, San Diego, Calif.). Recombinant pIFN-γ, used as a standard, was purchased from BioSource International (Camarillo, Calif.). Biotinylated mouse anti-pIFN-γ MAb P2C11 (BD Pharmingen) was used as the detecting antibody at a final concentration of 1 μg/ml. The concentration of pIFN-γ in the plasma was determined by extrapolation from a standard curve.

All animals in the control group developed clinical signs of disease by 2 dpc and had a significant lesion score (Table 5). Two of three animals in the groups that received a low dose of pIFN-α (group 2) or the lower dose of pIFN-γ (group 3) had delayed clinical signs. In contrast, the groups given the high dose of pIFN-γ alone (group 4) or pIFN-α combined with high-dose pIFN-γ (group 6) never developed any clinical disease. Most strikingly, the group given the combination of pIFN-α and the lower dose of pIFN-γ (group 5), which individually only delayed the onset of clinical disease, resulted in the complete inhibition of vesicular lesions.

TABLE 5

Clinical outcome of swine inoculated with Ad5s and challenged with FMDV.

| Gp. | Inoculum | Dose (PFU)[a] | Animal | Viremia (dpc, day of onset, duration [days][b] | No. of PFU from nasal swab specimen (dpc, day of onset, duration [days][c] | No. of lesions (day of onset)[d] |
|---|---|---|---|---|---|---|
| 1 | Ad5-VSVG[e] | $1 \times 10^{10}$ | 62 | $3.5 \times 10^6$ (4, 1, 6) | $1.5 \times 10^4$ (5, 3, 5) | 13 (2) |
| | | | 63 | $1.9 \times 10^6$ (4, 2, 5) | $1.8 \times 10^4$ (5, 3, 5) | 14 (2) |
| | | | 64 | $4.8 \times 10^6$ (4, 2, 5) | $1.4 \times 10^4$ (5, 3, 5) | 11 (2) |
| 2 | Ad5-Cl-pIFNα[f] | $1 \times 10^8$ | 65 | $1.2 \times 10^5$ (5, 4, 3) | $1.4 \times 10^3$ (6, 3, 5) | 8 (6) |
| | Ad5-VSVG | $1 \times 10^{10}$ | 66 | $6.9 \times 10^5$ (5, 4, 3) | $1.7 \times 10^4$ (5, 3, 5) | 10 (5) |
| | | | 67 | $2.5 \times 10^5$ (3, 2, 3) | $2.0 \times 10^4$ (4, 3, 4) | 14 (2) |
| 3 | Ad5-Cl-pIFNγ[g] | $1 \times 10^9$ | 68 | $2.5 \times 10^5$ (3, 2, 3) | $2.1 \times 10^3$ (3, 2, 3) | 10 (3) |
| | Ad5-VSVG | $1 \times 10^{10}$ | 69 | $1.9 \times 10^5$ (5, 4, 3) | $1.9 \times 10^3$ (5, 4, 3) | 14 (6) |
| | | | 70 | $4.8 \times 10^5$ (3, 1, 4) | $2.5 \times 10^3$ (3, 2, 6) | 15 (2) |
| 4 | Ad5-Cl-pIFNγ | $1 \times 10^{10}$ | 71 | Neg.[h] | Neg. | Neg. |
| | | | 72 | Neg. | Neg. | Neg. |
| | | | 73 | Neg. | Neg. | Neg. |
| 5 | Ad5-Cl-pIFNα | $1 \times 10^8$ | 74 | Neg. | Neg. | Neg. |
| | Ad5-Cl-pIFNγ | $1 \times 10^9$ | 75 | Neg. | Neg. | Neg. |
| | Ad5-VSVG | $1 \times 10^{10}$ | 76 | Neg. | Neg. | Neg. |
| 6 | Ad5-Cl-pIFNα | $1 \times 10^8$ | 77 | Neg. | Neg. | Neg. |
| | Ad5-Cl-pIFNγ | $1 \times 10^{10}$ | 78 | Neg. | Neg. | Neg. |
| | | | 79 | Neg. | Neg. | Neg. |

[a]Dose of inoculum per animal expressed as number of PFU in 2 ml of PBS.

[b]Number of PFU per ml of whole blood. The dpc value is the day after challenge that the maximum level of viremia was detected; the onset value is first day postchallenge that viremia was detected; and the duration value is the number of days of viremia.

[c]Number of PFU per ml of nasal secretion. The dpc, onset, and duration values are as defined in footnote b.

[d]Number of toes with lesions plus the snout and tongue combined, if lesions were present. The maximum score is 17. The day of onset is the first day after challenge that lesions were detected.

[e]Ad5 containing the glycoprotein gene of VSV New Jersey.

[f]Ad5 containing the pIFNα gene.

[g]Ad5 containing the pIFNγ gene.

[h]Neg., negative (less than 5 PFU/ml).

Example 7

Serological Response and Effect of Ad5-CI-pIFN-Containing Viruses on Protection Against FMDV Serum samples were heated at 56° C. for 30 min, and aliquots were stored at −70° C. Sera were tested for the presence of neutralizing antibodies against FMDV in a plaque reduction neutralization assay (Mason et al., supra). Neutralizing titers were reported as the serum dilution yielding a 70% reduction in the number of plaques. Heparinized blood was collected on the day of challenge (0 dpc) and daily for the first 7 dpc, and aliquots were frozen at −70° C. Viremia was determined by a standard plaque assay of BHK-21 cells. Plasma was obtained by centrifugation of heparinized blood at 2,500 rpm for 10 min and examined for antiviral activity and for the level of pIFN-α and pIFN-γ by ELISA as described below. Nasal swab specimens were obtained on the day of challenge and daily for 7 days after challenge. Virus was isolated from the swab samples by duplicate inoculation of monolayers of IBRS-2 cells in 24-well plates. The monolayers were incubated at 37° C. with 5% $CO_2$ and examined at 24, 48, and 72 h for cytopathic effect. Negative samples were frozen and thawed, and a second passage was performed. For positive samples, titration was performed from the original samples by a standard plaque assay of BHK-21 cells.

Lysates of radiolabeled-FMDV A24-infected IBRS-2 cells were incubated with serum from a convalescent-phase, FMDV-infected bovine or with individual serum samples from 0- and 21-dpc swine and examined for the presence of antibodies specific to FMDV structural and NS polypeptides by radioimmunoprecipitation (RIP). After 60 min of incubation at RT, antibodies were precipitated with *Streptococcus aureus* protein G and eluted proteins were resolved by SDS-PAGE on a 15% gel and visualized by autoradiography.

Detection of anti-3ABC antibody in swine serum samples was carried out with a commercial ELISA kit (Ceditest FMDV-NS; Cedi Diagnostic B.V., Lelystad, The Netherlands) based on the protocol provided by the manufacturer. Eighty microliters of ELISA buffer was added first to each well of a dried assay plate. Twenty-microliter samples of each testing serum and of the negative-control solution, weakly positive standard solution, and positive standard solution were added to different wells of the plate. After overnight incubation (16 h) at RT, the plate was washed six times with 1× wash solution using a plate washer. Antibody-horseradish peroxidase (HRP) conjugate was added to the plate (100 μl/well), and the plate was incubated for 1 h at RT and washed as described above. Next, HRP chromogenic substrate solution was added to the plate (100 μl/well) and incubated for 20 min at RT. The reaction was terminated by the addition of stop solution (100 μl/well). The optical density (OD) at 450 nm of the reaction product in each well was determined with an ELISA reader (VersaMax; Molecular Devices, Sunnyvale, Calif.). The antibody level of each sample was expressed as percent inhibition (PI) as follows: 100−[100×(ODsample/ODmax)], where ODmax is the OD value of the negative-control wells (maximum value). A sample was considered positive for anti-3ABC antibody when its PI was greater than 50% (a cutoff determined by the manufacturer).

The amount of anti-3D antibody in serum samples was determined by using a liquid-phase-blocking ELISA based on a baculovirus-expressed FMDV 3D protein and biotinylated bovine anti-FMD immunoglobulin G as the detector antibody. The assay was carried out at RT, and all washes were done three times with PBST. Twenty-five microliters of test serum was mixed with 100 μl PBST containing purified 3D at a predetermined concentration. A 50-μl aliquot of this serum-3D mix was added in duplicate to a 96-well plate (Maxisorp; Nunc, Denmark) that had previously been coated with rabbit anti-3D antibody. The plate was incubated for 60 min and washed. Biotinylated bovine anti-FMD immunoglobulin G, at a predetermined concentration, was added to the plate (50 µl/well) for 60 min, and the plate was washed.

virus than the control animals. No virus was detected in the nasal swab specimens of the protected animals.

All animals in the groups that developed clinical disease had significant levels of FMDV-specific neutralizing antibodies at 21 dpc, while the protected groups had only very low levels of neutralizing antibody (Table 6).

TABLE 6

Antibody response against FMDV A24 in swine at 21 dpc.

| Gp | Inoculum | Animal | Neutralizing $PRN_{70}{}^a$ | VIAA[b] | 3D ELISA[c] | 3ABC ELISA | RIP |
|----|----------|--------|-----------------------------|---------|-------------|------------|-----|
| 1 | Ad5-VSVG[e] | 62 | 1,600 | + | +++ | +++ | +++ |
|   |          | 63 | 800   | + | +++ | +++ | +++ |
|   |          | 64 | 800   | + | +++ | +++ | +++ |
| 2 | Ad5-CI-pIFNα | 65 | 6,400 | + | +++ | +++ | +++ |
|   | Ad5-VSVG | 66 | 800   | + | +++ | +++ | +++ |
|   |          | 67 | 3,200 | + | +++ | +++ | +++ |
| 3 | Ad5-CI-pIFNγ | 68 | 1,600 | + | +++ | ++ | +++ |
|   | Ad5-VSVG | 69 | 6,400 | + | +++ | +++ | +++ |
|   |          | 70 | 1,600 | + | +++ | ++ | +++ |
| 4 | Ad5-CI-pIFNγ | 71 | 16 | − | − | − | − |
|   |          | 72 | 16 | − | − | − | − |
|   |          | 73 | 16 | − | − | − | − |
| 5 | Ad5-CI-pIFNα | 74 | 32 | − | − | − | − |
|   | Ad5-CI-pIFNγ | 75 | 16 | − | − | − | − |
|   |          | 76 | 16 | − | − | − | − |
| 6 | Ad5-CI-pIFNα | 77 | 16 | − | − | − | − |
|   | Ad5-CI-pIFNγ | 78 | 16 | − | − | − | − |
|   |          | 79 | 32 | − | − | − | − |

[a] The neutralizing antibody response is reported as the serum dilution yielding a 70% reduction in the number of plaques ($PRN_{70}$).
[b] VIAA, (virus infection-associated antigen [3D], agar gel immunodiffusion against 3D.
[c] −, negative; ++, positive; +++, highly positive Anti-biotin MAb-HRP conjugate was added (1:5,000 dilution in PBST, 50 µl/well; Jackson ImmunoResearch Laboratories, West Grove, Pa.) for 30 min, and the plate was washed. Finally, a chromogen HRP substrate solution, tetramethyl benzidine (Sigma, St. Louis, Mo.), was added to the plate (100 µl/well), and the reaction was developed for 10 min and terminated by the addition of an equal volume of 1 M $H_2SO_4$. The OD of the chromogenic reaction product at 450 nm was determined with an ELISA reader (VersaMax; Molecular Devices), and the average from duplicate wells with each sample was obtained. The antibody level of each sample was expressed as PI by means of the following formula: 100−[100×(ODsample/ODmax)], where ODmax is the value for diluent control wells. A sample was considered 3D antibody positive when its PI was greater than 20%.

All animals were assayed for their antiviral response as well as for the presence of pIFN-α and pIFN-γ in their plasma. None of the animals had detectable levels of antiviral activity or IFNs (data not shown).

Figure 3:
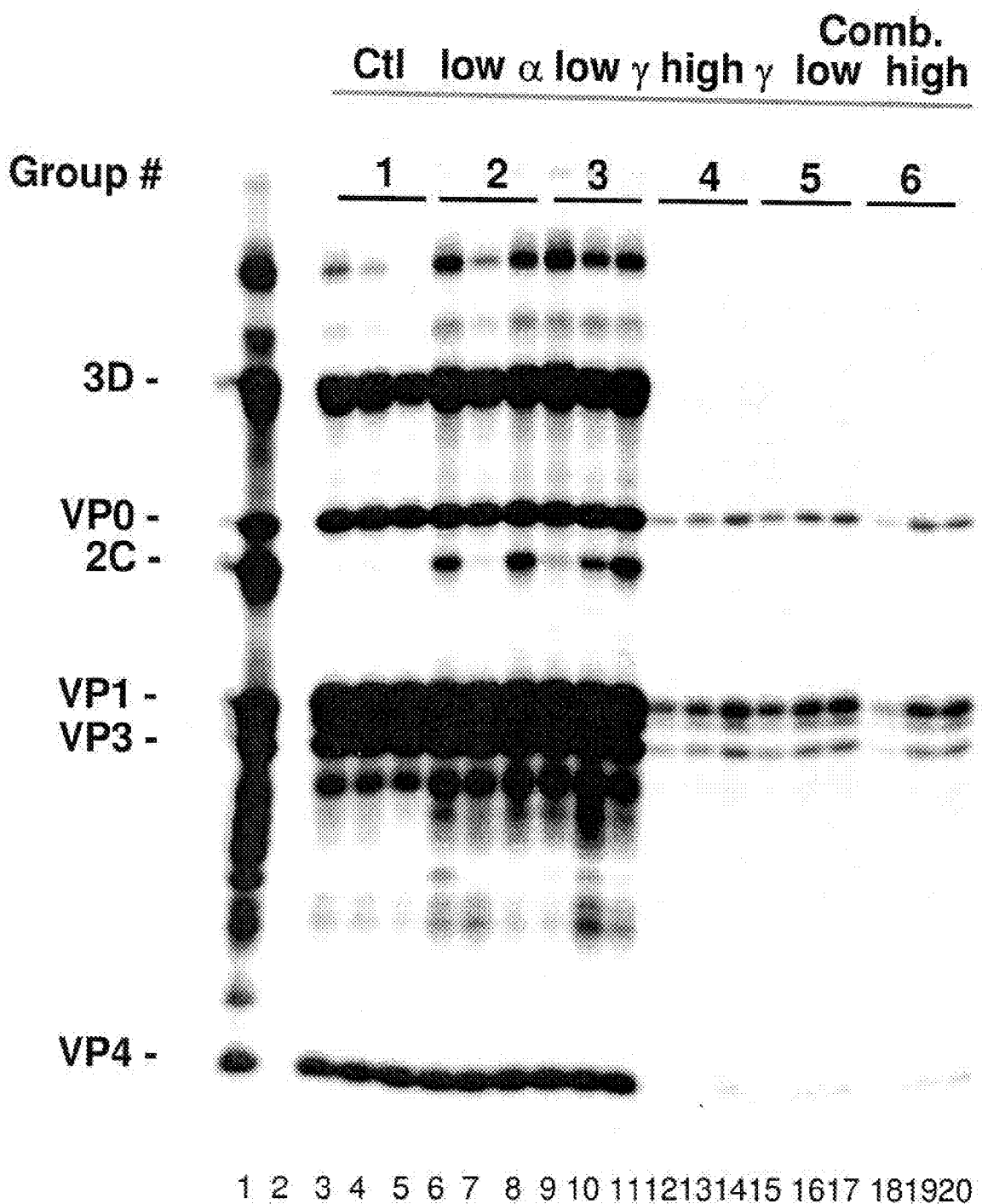
FIG. 3 shows the radioimmunoprecipitation (RIP) of FMDV A24-infected cell lysates with 21-dpc swine sera. [$^{35}$S]-methionine-labeled cell lysates from FMDV A24-infected IBRS-2 cells were immunoprecipitated with 21-dpc swine sera. Lane 1: bovine convalescent serum; lane 2: 0-dpc serum from swine 69; lanes 3-20: 21-dpc serum from swine 62-79 in the groups indicated in the figure. Immunoprecipitated samples were examined by sodium dodecyl sulfate-polyacrylamide gel electrophoresis (SDS-PAGE). Ctl, control; Comb., combination

The control group (group 1) developed viremia at 1 to 2 dpc (Table 5). Viremia lasted for 5 to 6 days and reached a peak of greater than $10^6$ PFU/ml. All the animals in the groups given only IFN-α (group 2) or the lower dose of IFN-γ (group 3) developed viremia, but viremia was delayed and lasted for a shorter period of time than in control animals and the titer of virus was generally 10-fold lower than that of the control group. The three groups that were protected from clinical disease (groups 4 to 6) never developed viremia. Virus was also detected in the nasal swab specimens of the control group and the groups given only IFN-α or the lower dose of IFN-γ, although the latter group had 5- to 10-fold-lower levels of All animals in the groups that developed clinical disease had antibodies at 21 dpc against viral NS proteins as detected by a number of assays, including ELISAs against 3D and 3ABC, a 3D agar gel immunodiffusion assay, and RIP (Table 6 and FIG. 3). In contrast, none of the protected animals showed evidence of induction of antibodies against viral NS proteins by these assays, while by RIP (FIG. 3) and the neutralization assay (Table 6) there was evidence of antibodies against the viral structural proteins.

Example 8

Genes Induced in Challenged Animals

Because of the large number of samples, we selected only groups 1, 2, 4, and 6 to examine the induction of IFN-stimulated genes (ISGs). As seen in Table 7, there was no statistically significant enhancement of any of the ISGs in groups 1 and 2, although there was a low level of induction of iNOS in group 2. The induction of IRF1 in group 2 was due to only one animal, no. 67. In group 4, given the high dose of Ad5-CI-pIFN-γ, there was an induction of INDO and IP-10 mRNA on days 1 and 2 postinoculation, but on day 3, these mRNAs were induced only in the animal that had the highest levels of induction on the other days, animal 71 (data not shown). In group 6, which was given the combination of Ad5-CI-pIFN-α and the high dose of Ad5-CI-pIFN-γ, there were statistically significant levels of induction of INDO and IP-10 mRNA compared to levels of induction in groups 1 and 2 (P<0.05). There was also a low-level, but consistent, induction of OAS in all three animals in group 6 on days 1 and 3. Furthermore, there was a synergistic increase in the level of induction of INDO and IP-10 mRNAs in this group compared to induction levels in groups 2 and 4. As we have previously observed, the standard deviation for these mRNAs was large because of the variations in the responses in outbred animals (de Avila Botton et al., supra); nevertheless, each animal in group 6 had a significant induction of INDO and IP-10 mRNAs on all 3 days examined (data not shown).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

TABLE 7

Induction of IFN-stimulated Genes in Swine White Blood Cells.

| $G^a$ | Day p.i. | IFN-α | IFN-β | IFN-γ | INDO | iNOS | IP-10 | IRF1 | Mx1 | OAS | PKR | RANTES |
|---|---|---|---|---|---|---|---|---|---|---|---|---|
| 1 | 1 | 0.7 ± 0.4 | 27.4 ± 35.7 | 1.8 ± 0.4 | 1.9 ± 1.7 | 0.4 ± 0.2 | 2.8 ± 2.0 | 0.6 ± 0.2 | 2.5 ± 0.9 | 1.4 ± 1.2 | 0.9 ± 0.2 | 0.4 ± 0.2 |
|   | 2 | 0.6 ± 0.3 | 2.2 ± 2.2 | 1.0 ± 0.5 | 0.7 ± 0.1 | 0.4 ± 0.2 | 0.2 ± 0.1 | 0.6 ± 0.1 | 1.3 ± 0.4 | 0.8 ± 0.2 | 0.9 ± 0.2 | 0.7 ± 0.1 |
|   | 3 | 0.4 ± 0.1 | 5.6 ± 3.8 | 1.2 ± 0.3 | 1.5 ± 1.1 | 0.3 ± 0.1 | 4.3 ± 3.0 | 0.7 ± 0.6 | 2.5 ± 1.7 | 1.9 ± 0.4 | 1.1 ± 0.6 | 0.5 ± 0.2 |
| 2 | 1 | 0.9 ± 1.0 | 0.1 ± 0.1 | 0.5 ± 0.4 | 0.1 ± 0.1 | 1.5 ± 1.1 | 0.2 ± 0.1 | 10.4 ± 14.8 | 0.7 ± 0.2 | 1.6 ± 1.8 | 0.4 ± 0.1 | 0.5 ± 0.5 |
|   | 2 | 1.6 ± 1.2 | 0.1 ± 0.1 | 1.8 ± 1.2 | 0.1 ± 0.0 | 3.4 ± 2.5 | 0.1 ± 0.1 | 6.4 ± 6.4 | 0.8 ± 0.5 | 1.8 ± 1.4 | 0.7 ± 0.6 | 0.7 ± 0.4 |
|   | 3 | 1.5 ± 1.7 | 0.0 ± 0.0 | 1.1 ± 0.4 | 0.0 ± 0.0 | 2.4 ± 0.7 | 0.0 ± 0.0 | 18.6 ± 24.8 | 0.2 ± 0.0 | 0.8 ± 0.6 | 0.4 ± 0.1 | 1.0 ± 0.4 |
| 4 | 1 | 0.6 ± 0.3 | 2.8 ± 3.2 | 1.1 ± 0.6 | 15.8 ± 17.5 | 0.2 ± 0.1 | 13.0 ± 10.3 | 1.2 ± 0.5 | 1.0 ± 1.2 | 1.5 ± 1.6 | 0.5 ± 0.3 | 0.4 ± 0.2 |
|   | 2 | 1.2 ± 0.6 | 0.4 ± 0.3 | 0.9 ± 0.6 | 9.4 ± 7.9 | 0.3 ± 0.3 | 2.8 ± 2.1 | 1.1 ± 0.3 | 0.2 ± 0.2 | 0.4 ± 0.3 | 0.3 ± 0.1 | 0.9 ± 0.1 |
|   | 3 | 1.2 ± 0.5 | 38.6 ± 52.6 | 5.9 ± 5.4 | 39.4 ± 53.7 | 0.7 ± 0.7 | 9.9 ± 12.9 | 2.9 ± 2.4 | 0.8 ± 0.9 | 2.5 ± 2.3 | 0.6 ± 0.4 | 1.6 ± 0.5 |
| 6 | 1 | 1.4 ± 0.8 | 3.1 ± 1.4 | 0.3 ± 0.1 | 40.3 ± 8.9$^d$ | 0.4 ± 0.1 | 49.2 ± 23.6$^d$ | 1.8 ± 0.8 | 1.8 ± 0.5 | 4.2 ± 1.8 | 1.0 ± 0.3 | 0.5 ± 0.1 |
|   | 2$^c$ | 0.6 ± 0.2 | 0.6 ± 0.5 | 0.3 ± 0.1 | 40.2 ± 21.3 | 0.2 ± 0.0 | 21.8 ± 7.9 | 0.9 ± 0.4 | 0.6 ± 0.0 | 2.7 ± 2.1 | 0.3 ± 0.0 | 0.5 ± 0.1 |
|   | 3 | 4.7 ± 3.1 | 32.0 ± 32.0 | 1.8 ± 0.7 | 47.6 ± 27.9 | 1.5 ± 1.0 | 15.4 ± 5.1 | 2.4 ± 1.0 | 1.4 ± 0.5 | 5.6 ± 2.3 | 0.9 ± 0.3 | 1.9 ± 0.6 |

$^a$Group 1 was inoculated with Ad5-VSVG, group 2 was inoculated with $10^8$ PFU of Ad5-Cl-pIFN-α, group 4 was inoculated with $10^{10}$ PFU of Ad5-Cl-pIFN-γ, and group 6 was inoculated with $10^8$ PFU of Ad5-Cl-pIFN-α and $10^{10}$ PFU of Ad5-Cl-pIFN-γ.
$^b$Data are means ± standard deviations from three samples.
$^c$There was no sample for one of the three animals in this group on day 2 postinoculation.
$^d$There was a statistically significant induction of INDO and IP-10 in group 6 compared to levels of induction in groups 1 and 2 ($P < 0.05$).

We claim:

1. An effective anti-foot and mouth disease virus (FMDV) vaccine comprising an effective amount of a porcine IFN-γ (pIFN-γ) gene and a porcine IFN-α (pIFN-α) gene wherein said combination of pIFN-γ and pIFN-α acts synergistically to block FMDV replication in vivo and protects animals susceptible to FMDV from clinical disease.

2. The vaccine of claim 1, wherein said vaccine comprises an effective amount of a viral gene transfer vector wherein said vector is an adenovirus and wherein said vector comprises a nucleic acid construct capable of expressing said pIFN-γ gene and an additional viral gene transfer vector wherein said additional vector is an adenovirus and wherein said additional vector comprises a nucleic acid construct capable of expressing said pIFN-α gene.

3. The vaccine of claim 2 wherein a single viral gene transfer vector contains both the nucleic acid construct capable of expressing the pIFN-γ gene and the nucleic acid construct capable of expressing the pIFN-α gene.

4. The vaccine of claims 1 wherein the animals susceptible to FMDV are swine, cattle, goats, or sheep.

5. A method of protecting susceptible animals from foot and mouth disease comprising:
administering to said animals an effective dosage of a vaccine comprising an effective amount of a pIFN-γ gene and a pIFN-α gene wherein said combination of pIFN-γ and pIFN-α acts synergistically to block FMDV replication in vivo and protects animals susceptible to FMDV from clinical disease.

6. The method of protecting susceptible animals from FMD of claim 5, wherein said vaccine comprises an effective amount of a viral gene transfer vector wherein said vector is an adenovirus and wherein said vector comprises a nucleic acid construct capable of expressing said pIFN-γ gene and an additional viral gene transfer vector wherein said additional vector is an adenovirus and wherein said additional vector comprises a nucleic acid construct capable of expressing said pIFN-α gene.

7. The method of claim 6 wherein a single viral gene transfer vector contains both the nucleic acid construct capable of expressing the pIFN-γ gene and the nucleic acid construct capable of expressing the pIFN-α gene.

8. The method of claim 5 wherein said animals susceptible to FMD are swine, cattle, goats, or sheep.

9. A method of synergistically inducing INDO and IP-10 in animals susceptible to FMDV comprising:
administering to said animals an effective dosage of a vaccine, wherein said vaccine comprises an effective amount of a viral gene transfer vector wherein said vector is an adenovirus and wherein said vector comprises a nucleic acid construct capable of expressing said pIFN-γ gene and an additional viral gene transfer vector wherein said additional vector is an adenovirus and wherein said additional vector comprises a nucleic acid construct capable of expressing said pIFN-α gene.

* * * * *